(12) United States Patent  (10) Patent No.: US 7,550,627 B2
Lavoie et al.  (45) Date of Patent: Jun. 23, 2009

(54) PROCESSES FOR PRODUCING AROMATIC DICARBOXYLIC ACIDS

(75) Inventors: Gino Georges Lavoie, Kingsport, TN (US); Robert Thomas Hembre, Johnson City, TN (US); Charles Edwan Sumner, Jr., Kingsport, TN (US); Joseph Nathaniel Bays, Kingsport, TN (US); Daniel Burts Compton, Kingsport, TN (US); Brent Alan Tennant, Kingsport, TN (US); Bryan Wayne Davenport, Columbia, SC (US); David Lange, Irmo, SC (US); Thomas Richard Floyd, Kingsport, TN (US)

(73) Assignee: Eastman Chemical Company, Kingsport, TN (US)

( * ) Notice: Subject to any disclaimer, the term of this patent is extended or adjusted under 35 U.S.C. 154(b) by 454 days.

(21) Appl. No.: 11/075,009

(22) Filed: Mar. 8, 2005

(65) Prior Publication Data

US 2006/0205975 A1 Sep. 14, 2006

(51) Int. Cl.
*C07C 51/16* (2006.01)
*C07C 63/00* (2006.01)
(52) U.S. Cl. ..................... 562/413; 562/480
(58) Field of Classification Search ........... 562/413, 562/487, 480
See application file for complete search history.

(56) References Cited

U.S. PATENT DOCUMENTS 2,833,816 A  5/1958 Saffer et al.
2,962,361 A  11/1960 Spiller, Jr. et al.
3,012,038 A  12/1961 O'Neill et al.
3,089,906 A  5/1963 Saffer et al.
3,299,125 A  1/1967 Ichikawa
3,513,192 A  5/1970 Lumbroso
3,562,318 A  2/1971 Barone et al.
3,607,919 A  9/1971 Barone (Continued)

FOREIGN PATENT DOCUMENTS

CN  1486968 A  4/2004

(Continued)

OTHER PUBLICATIONS

Notification of Transmittal of the International Search Report and the Written Opinion of the International Searching Authority, or the Declaration date of mailing Jul. 5, 2006 received on the PCT filing of U.S. Appl. No. 11/075,009 filed Mar. 8, 2005.

(Continued)

*Primary Examiner*—Taylor Victor Oh
(74) *Attorney, Agent, or Firm*—Steven A. Owen; Dennis V. Carmen; Bernard J. Graves, Jr.

(57) ABSTRACT

Processes for producing aromatic dicarboxylic acids are disclosed, the processes including a step of combining in a reaction medium a dialkyl aromatic, a solvent comprising water and a saturated organic acid having from 2-4 carbon atoms, and an oxygen-containing gas, at a temperature from about 125° C. to about 155° C., in the presence of a catalyst composition comprising cobalt, manganese, zirconium, and bromine, wherein the weight ratio of cobalt to manganese in the reaction mixture is from about 10 to about 400. The processes provide improved conversion, while reducing the formation of carbon oxides and other by-products.

25 Claims, 1 Drawing Sheet

U.S. PATENT DOCUMENTS

| | | | |
|---|---|---|---|
| 3,781,344 A | 12/1973 | Alagy et al. | |
| 3,839,435 A | 10/1974 | Shigeyasu et al. | |
| 3,920,735 A | 11/1975 | Wampfler et al. | |
| 3,931,304 A | 1/1976 | Wampfler | |
| 3,950,409 A | 4/1976 | Yokota et al. | |
| 3,970,696 A | 7/1976 | Shigeyasu et al. | |
| 3,996,271 A | 12/1976 | Yokota et al. | |
| 4,017,547 A | 4/1977 | Simmons et al. | |
| 4,051,178 A | 9/1977 | Kimura et al. | |
| 4,140,722 A | 2/1979 | Williams et al. | |
| 4,158,738 A | 6/1979 | Scott et al. | |
| 4,159,307 A | 6/1979 | Shigeyasu et al. | |
| 4,160,108 A | 7/1979 | Shigeyasu et al. | |
| 4,197,412 A | 4/1980 | Kimura et al. | |
| 4,230,882 A | 10/1980 | Seko et al. | |
| 4,241,220 A | 12/1980 | Itaya et al. | |
| 4,243,636 A | 1/1981 | Shiraki et al. | |
| 4,314,073 A * | 2/1982 | Crooks | 562/416 |
| 4,327,226 A | 4/1982 | Shigeyasu et al. | |
| 4,354,037 A | 10/1982 | Hirose et al. | |
| 4,370,496 A | 1/1983 | Shigeyasu et al. | |
| 4,447,646 A | 5/1984 | Johnson et al. | |
| 4,447,647 A | 5/1984 | Werner et al. | |
| 4,501,781 A | 2/1985 | Kushida et al. | |
| 4,593,122 A | 6/1986 | Hasizume et al. | |
| 4,605,763 A | 8/1986 | Kiefer et al. | |
| 4,719,311 A | 1/1988 | Partenheimer | |
| 4,786,753 A | 11/1988 | Partenheimer et al. | |
| 4,800,129 A | 1/1989 | Deak | |
| 4,826,955 A | 5/1989 | Akkapeddi et al. | |
| 4,827,025 A | 5/1989 | Shiraki et al. | |
| 4,853,479 A | 8/1989 | Dakka et al. | |
| 4,855,491 A | 8/1989 | Chew et al. | |
| 4,877,900 A | 10/1989 | Tamaru et al. | |
| 4,892,970 A | 1/1990 | Nowicki et al. | |
| 4,992,580 A | 2/1991 | Partenheimer | |
| 5,021,515 A | 6/1991 | Cochran et al. | |
| 5,049,624 A | 9/1991 | Adams et al. | |
| 5,112,992 A | 5/1992 | Belmonte et al. | |
| 5,159,005 A | 10/1992 | Frandsen et al. | |
| 5,166,420 A | 11/1992 | Shiraki et al. | |
| 5,194,478 A | 3/1993 | Frandsen et al. | |
| 5,281,360 A | 1/1994 | Hong et al. | |
| 5,292,934 A | 3/1994 | Sikkenga et al. | |
| 5,324,702 A | 6/1994 | Yoo et al. | |
| 5,359,133 A | 10/1994 | Nazimok et al. | |
| 5,359,134 A | 10/1994 | Gustafson et al. | |
| 5,371,283 A | 12/1994 | Kingsley et al. | |
| 5,510,521 A | 4/1996 | McGehee et al. | |
| 5,523,474 A | 6/1996 | Kingsley et al. | |
| 5,536,875 A | 7/1996 | Roby et al. | |
| 5,679,847 A | 10/1997 | Ohkoshi et al. | |
| 5,696,285 A | 12/1997 | Roby | |
| 5,744,246 A | 4/1998 | Ching | |
| 5,756,833 A | 5/1998 | Rosen et al. | |
| 5,759,653 A | 6/1998 | Collette et al. | |
| 5,763,648 A | 6/1998 | Hashizume et al. | |
| 5,763,833 A | 6/1998 | Bawa et al. | |
| 5,847,203 A | 12/1998 | Pennington et al. | |
| 6,153,790 A | 11/2000 | June et al. | |
| 6,160,170 A | 12/2000 | Codignola | |
| 6,239,210 B1 | 5/2001 | Kim et al. | |
| 6,255,525 B1 | 7/2001 | Sikkenga et al. | |
| 6,288,161 B1 | 9/2001 | Kim et al. | |
| 6,307,099 B1 | 10/2001 | Turner et al. | |
| 6,410,156 B1 | 6/2002 | Akkapeddi et al. | |
| 6,455,620 B1 | 9/2002 | Cyr et al. | |
| 6,476,257 B1 | 11/2002 | Park et al. | |
| 6,504,051 B1 | 1/2003 | Miller, Jr. et al. | |
| 6,620,966 B2 | 9/2003 | Ohkoshi et al. | |
| 6,649,773 B2 | 11/2003 | Colborn et al. | |
| 6,670,502 B1 | 12/2003 | Codignola | |
| 2002/0183546 A1 | 12/2002 | Sheppard et al. | |
| 2002/0193629 A1 | 12/2002 | Miller, Jr. et al. | |
| 2002/0193630 A1 | 12/2002 | Lin et al. | |
| 2004/0015009 A1 | 1/2004 | Earle et al. | |
| 2004/0241468 A1 | 12/2004 | Otaki | |

FOREIGN PATENT DOCUMENTS

| | | |
|---|---|---|
| DE | 2420805 A | 11/1975 |
| EP | 0 041 784 A1 | 12/1981 |
| EP | 0 673 910 A1 | 9/1995 |
| GB | 1 347 943 | 2/1974 |
| GB | 1 389 478 | 4/1975 |
| JP | 48-096545 | 12/1973 |
| JP | 52-077023 A | 6/1977 |
| JP | 55-17348 A | 2/1980 |
| JP | 1997278709 A | 10/1997 |
| JP | 2001139514 | 5/2001 |
| JP | 2001288139 | 10/2001 |
| JP | 2001247511 | 11/2001 |
| KR | 2000-0001634 A | 1/2000 |
| PL | 134127 B1 | 7/1985 |
| PL | 144072 B1 | 4/1988 |
| WO | WO 94/04480 | 3/1994 |
| WO | WO 94/04481 | 3/1994 |
| WO | WO 95/09143 | 4/1995 |
| WO | WO 98/29378 | 7/1998 |
| WO | WO 99/31038 | 6/1999 |
| WO | WO 00/37406 | 6/2000 |
| WO | WO 00/66529 | 11/2000 |
| WO | WO 01/3821 A1 | 5/2001 |
| WO | WO 01/38279 A1 | 5/2001 |
| WO | WO 01/38280 A1 | 5/2001 |
| WO | WO 01/38282 A1 | 5/2001 |
| WO | WO 2005/000779 A2 | 1/2005 |

OTHER PUBLICATIONS

Abramovitch, R. A.; "Polar Radicals in Aromatic Substitution"; Intra-Science Chemistry Reports; 1969; 211-218; vol. 3.

Dumitriu, D. et al.; "$BiO_x$ Clusters Occluded in a ZAM-5 Matrix: Preparation, Characterization, and Catalytic Behavior in Liquid-Phase Oxidation of Hydrocarbons"; Journal of Catalysis; 2003; 337-351; 219.

Bezhanishvili, G. S. and Nezdominov, V. A.; "Improving the Terephthalic Acid Production Process"; Neftepereabotka i neftekhimiya; 1983; 39-40; 4.

Cavalieri D'Oro, P., Danoczy, E. and Roffia, P.; "On the Low Temperature Ozidation of p-Xylene"; Oxidation Communications 1, 1980; 153-162; 2.

Chester, Arthur W., Scott, Eric J. Y. and Landis, Phillip S.; "Zirconium Cocatalysis of the Cobalt-Catalyzed Autoxidation of Alkylaromatic Hydrocarbons"; Journal of Catlysis; 1977; 308-319; 46.

Fossey, J.; Lefort, D. and Sorba, J.; "Free Radicals in Organic Chemistry"; 1995; 148-150; John Wiley & Sons.

Katritzky, Alan R. et al., "Reactions of the 1-Amino-2,4,6-Triphenylpyridinium Cation"; J. Chem. Research; 1982; 208-209.

"Phthalic Acids and Other Benzenepolycarboxylic Acids"; Kirk-Othmer Encyclopedia of Chemical Technology; 1995; 991-1043; vol. 18, $4^{th}$ ed.

Okada, Toshihiko and Kamiya, Yoshio; "The Oxidation of Toluene by Cobalt-Copper-Bromide System. A Side-Chain Acetoxylation"; Bulletin of the Chemical Society of Japan; 1979; 3321-3325; vol. 52 (11).

Partenheimer, Walt; "Characterization of the Reaction of Cobalt (II), Acetate, Dioxygen and Acetic Acid, and Its Significance in Autoxidation Reactions"; Journal of Molecular Catalysis; 1991; 35-46; vol. 67.

Pokrovskaya, Romanova, Bashurina, Eremeev and Makarova; Neftekhimiya; 1978; 565-572; 18(4); (English language abstract from SciFinder, text in Russian).

Saha, Basaudeb and Espenson, James H.; "Bromoanthracenes and Metal Co-Catalysts for the Autoxidation of Para-Xylene"; Journal of Molecular Catalysis A: Chemical; 2004; 121-127; 207.

Srivastava, Krishna K. and Chandalia, Sampatraj B.; "Liquid Phase Oxidation of p-Xylene to Terephthalic Acid by Air in the Absence of a Promoter"; J. Chem. Tech. Biotechnol.; 1981; 609-614; vol. 31.

V. Ramakrishna, Shashi Anand and Vasudevan, Padma; "Oxidation of Xylenes by Bismuthoxide-Molybdenum Oxide Catalysts"; J. Indian Chem. Soc.; 1979; 877-879; vol. LVI.

Co-pending U.S. Appl. No. 11/214,406, filed Aug. 29, 2005.

Co-pending U.S. Appl. No. 11/075,008, filed Mar. 8, 2005.

* cited by examiner

FIGURE 1

PROCESSES FOR PRODUCING AROMATIC DICARBOXYLIC ACIDS

FIELD OF THE INVENTION

This invention pertains to improved processes for the production of aromatic dicarboxylic acids by the liquid-phase oxidation of dialkyl aromatic hydrocarbons, the processes resulting in improved conversion, while reducing formation of carbon oxides and other by-products.

BACKGROUND OF THE INVENTION

Aromatic dicarboxylic acids such as terephthalic acid and isophthalic acid are used to produce a variety of polyester products, important examples of which are poly(ethylene terephthalate) and its copolymers. These aromatic dicarboxylic acids may be synthesized by the catalytic oxidation of the corresponding dialkyl aromatic compound. For example, terephthalic acid (TPA) and isophthalic acid (IPA) may be produced by the liquid phase oxidation of p-xylene and m-xylene, respectively.

These processes typically comprise feeding one or more dialkyl aromatic hydrocarbons, fresh and/or recycled solvent or reaction medium, and catalyst components to a reactor to which a molecular oxygen-containing gas also is fed, typically near the bottom of the reactor. Conventional liquid-phase oxidation reactors are equipped with agitation means for mixing the multi-phase reaction medium. Agitation of the reaction medium is supplied in an effort to promote dissolution of molecular oxygen into the liquid phase of the reaction medium, and to facilitate contact between the dissolved oxygen and the dialkyl aromatic hydrocarbon in the reaction medium. Agitation of the reaction medium undergoing liquid-phase oxidation is frequently provided by mechanical agitation means in vessels such as, for example, continuous stirred tank reactors (CSTRs). Bubble column reactors provide an attractive alternative to CSTRs and other mechanically agitated oxidation reactors.

In these processes, bubble column reactors may be used having relatively high height to diameter ratios. The oxygen-containing process gas rising through the liquid contents of the reactor results in agitation of the reaction mixture. Alternatively, continuous stirred tank reactors may be used, typically having a lower height to diameter ratio than bubble column reactors. The aromatic dicarboxylic acid produced may be removed continuously through an exit port as a slurry. Process gas containing excess oxygen, along with solvent decomposition products, may be removed through an upper exit port typically located at or near the top of the reactor. The heat of reaction may also be removed through the upper exit port by vaporization of the process solvent and water generated by the reaction.

Thus, in one example of such a process, p-xylene is oxidized to produce terephthalic acid. The p-xylene may be continuously or batchwise oxidized in the primary oxidation reactor in the liquid phase, in the presence of an oxygen-containing gas such as air. In such a process, p-xylene, an oxidation catalyst composition, a molecular source of oxygen, and a solvent such as aqueous acetic acid are combined as a reaction medium in the reactor to produce a crude terephthalic acid (CTA) reaction product. Typical oxidation catalyst compositions include a cobalt compound and a manganese compound, usually in combination with a promoter such as a bromine compound. See, for example, U.S. Pat. Nos. 2,833, 816, 3,089,906, and 4,314,073, the disclosures of which are incorporated herein by reference. The process conditions are highly corrosive due to the acetic acid and bromine, and titanium is typically used in the process equipment. See, for example, U.S. Pat. No. 3,012,038, incorporated herein by reference. Acetaldehyde may be used as a promoter in place of bromine, in which case titanium materials need not be used. Acetaldehyde is also useful as an initiator. Because the liquid-phase oxidations of dialkyl aromatic compounds just described are highly exothermic reactions, they are commonly carried out in vented reaction vessels, the heat of reaction being removed by vaporization of the process solvent through the upper exit port.

The resulting CTA is not very soluble in the acetic acid solvent under the reaction conditions, and precipitates from the solvent to form a suspension. This crude terephthalic acid suspension includes terephthalic acid solids, a solvent acting as the suspending medium for the solids and containing a small amount of dissolved terephthalic acid; catalyst components; unreacted p-xylene; incompletely oxidized intermediate oxidation products such as para-tolualdehyde (p-TA1), para-toluic acid (p-TA), and 4-carboxybenzaldehyde (4-CBA); and organic impurities such as fluorenones that are known to cause discoloration. The crude terephthalic acid composition is discharged from the oxidation zone and subjected to any of several mother liquor exchange, separation, purification, or recovery methods, with the recovered solvent and catalyst composition being recycled directly back to the oxidation reaction or after processing, such as by catalyst recovery or solvent purification. It is desirable to minimize the amount of incompletely oxidized intermediates and the colored impurities, to reduce the subsequent purification requirements.

Other by-products of the liquid phase oxidation which are partially or completely removed from the reaction mixture in the oxidation reactor are the off-gases, which include water, solvent, unreacted oxygen and other unreacted gases found in the source of the molecular oxygen gas such as nitrogen and carbon dioxide, and additional amounts of carbon dioxide and carbon monoxide that are oxidative losses resulting in part from the catalytic decomposition of the solvent and other oxidizable compounds under the oxidation conditions. The off-gases are vented at the overhead of the oxidation reactor to a distillation column or a condenser to separate the solvent from the other off-gases such as water, carbon dioxide, carbon monoxide, nitrogen, gaseous bromine compounds such as methyl bromide, etc.

Although it is desirable to recover and recycle as much solvent as possible, the solvent is oxidatively decomposed to some extent into its constituent gaseous products, carbon dioxide and carbon monoxide, requiring a fresh source of make-up solvent. This oxidative decomposition is often referred to in the industry as solvent burn or acid burn, and is generally believed to be responsible in part for the formation of carbon oxides, although a portion of the carbon oxides produced is also the result of oxidative decomposition of the dialkyl aromatics or intermediate reaction products. Controlling or reducing formation of carbon oxides would significantly lower the operating costs of the oxidation process, by allowing a greater amount of solvent to be recovered and recycled back to the oxidation zone, and possibly also by reducing yield loss from the oxidative decomposition of the aromatic reactants. However, a reduction in carbon oxides formation should not come at the expense of significantly reduced yield or conversion, or an increase in the amount of incomplete oxidation products in the crude mixture, and if possible, it would be desirable to simultaneously reduce carbon oxides formation and increase the conversion. Typically, however, increased conversion is accompanied by an increase in carbon oxides formation.

U.S. Pat. No. 3,920,735 discloses a method of oxidizing di- or trimethylbenzenes with molecular oxygen to form benzene di- or tri-carboxylic acids under liquid phase conditions using catalyst systems that include cobalt, bromine, and zirconium; or cobalt, manganese, bromine, and zirconium. According to the disclosure, these catalyst systems must contain at least 20 percent manganese.

G. S. Bezhanishvili and V. A. Nezdominov, *Neftepererabotka I Neftekhimiya* (*Moscow, Russian Federation*) 1983, 4, 39-40, studied the effects of the addition of manganese and zirconium on a cobalt-bromide catalyst used for the oxidation of para-xylene at atmospheric pressure and temperatures less than 100° C.

U.S. Pat. No. 4,992,580 discloses that the addition of molybdenum to an oxidation catalyst system that includes cobalt increases the catalytic activity of the catalyst system. The molybdenum is said to activate the cobalt moiety.

U.S. Pat. No. 5,359,133 discloses a multi-stage process for producing benzenedicarboxylic acid isomers that includes an oxidation step wherein xylene isomer is partially oxidized with molecular oxygen or molecular oxygen-containing gas in the presence of a catalyst system composed of cobalt, manganese, bromine, and at least one selected from nickel, chromium, zirconium and cerium in lower aliphatic carboxylic acid.

PCT Publn. No. WO 00/37406 discloses the liquid phase oxidations of alkyl aromatic hydrocarbons, using oxygen-enriched gas, in the presence of a catalyst of cobalt, manganese, and bromide, and one or more than one type of transition metal or lanthanide metal component.

PCT Publn. No. WO 00/66529 discloses that the use of a feed gas containing both oxygen and carbon dioxide for the oxidation of alkyl aromatic substrates or their partially oxidized intermediates to produce carboxylic acid products improves the yield and quality of the resulting product. The carbon dioxide is said to function as a co-oxidant along with oxygen. The document suggests that in addition to a catalyst system comprising cobalt, manganese, and bromine, an additional transition metal or lanthanide series metal may be introduced when deemed necessary.

There remains a need in the art for aromatic oxidation processes that achieve improved conversion, while minimizing carbon oxides formation. These and additional advantages are obtained by the present invention, as further described below.

SUMMARY OF THE INVENTION

The invention relates to processes for producing one or more aromatic dicarboxylic acids, and especially terephthalic acid, the processes comprising combining in a reaction medium a dialkyl aromatic such as p-xylene, an aqueous solvent comprising one or more saturated organic acids having from 2-4 carbon atoms, and an oxygen-containing gas, at a temperature from about 125° C. to about 155° C., in the presence of a catalyst composition comprising cobalt atoms, manganese atoms, zirconium atoms, and bromine atoms, wherein the weight ratio of cobalt to manganese is from about 10 to about 400.

We have unexpectedly discovered according to the invention that when zirconium is added to a catalyst composition comprising cobalt, manganese, and bromine, improved conversion is obtained at moderate temperatures without an unacceptable increase in carbon oxides formation.

DETAILED DESCRIPTION OF THE INVENTION

The present invention may be understood more readily by reference to the following detailed description of the invention, including the appended figure, and to the examples provided. It is to be understood that the terminology used is for the purpose of describing particular embodiments only and is not intended to be limiting.

As used in the specification and the claims, the singular forms "a," "an," and "the" include plural referents unless the context clearly dictates otherwise. Thus, when the disclosure and the claims use the phrase "a dialkyl aromatic," the phrase is intended to encompass one or more dialkyl aromatics. Similarly, when the phrase "an organic acid having from 2-4 carbon atoms" is used, for example, the phrase is intended to encompass one or more such organic acids.

It is to be understood that the words "comprising" and "containing" are open ended and may include any number and type of unstated steps, processes, or ingredients. The description of method steps does not preclude intervening steps and is not restricted to carrying out the steps in a particular order unless otherwise stated. Numerical ranges include each integer and all fractions thereof between the end points of the stated range.

Unless otherwise indicated, the weight amount of catalyst is based in each instance on the total weight of the liquid in the reaction medium, without regard to the amount of precipitated product in the reaction medium, the amount of which may change during the course of the reaction, especially in those cases in which the process is carried out as a batch or semi-batch process. The defined weight amounts may be determined by removal of a portion of the reaction medium either during or after the reaction, since the amount present in the reaction mixture may differ somewhat from the concentration of catalyst as initially provided to the reaction mixture, due to evaporation, solvent burn, etc.

According to the invention, the extent of carbon oxides formation, in part a result of oxidative loss of solvent, observed, for example, in the oxidation of p-xylene to terephthalic acid, is minimized by the use of moderate reaction temperatures with weight ratios of cobalt to manganese of at least about 10. We have discovered that the use of catalyst compositions according to the invention, at moderate reaction temperatures, improves the conversion with a concomitant decrease in impurities generation rate, such as that for benzoic acid, which in turn is a good indicator of other undesirable impurities. The use of the catalyst compositions according to the invention also leads to low quantities of CO and $CO_2$ produced in the course of the reaction, which is believed to be a good indicator of the extent of acid burn. Such a decrease in carbon oxides formation in the oxidation of p-xylene translates into significant cost savings in the manufacture of terephthalic acid, by reducing for example the extent of acid burn. Remarkably, at these moderate temperatures, the addition of zirconium improves conversion while having very little impact on carbon oxides formation.

Thus, according to the invention, one or more dialkyl aromatics, provided as a liquid, preferably a xylene, and especially p-xylene, is oxidized in an aqueous aliphatic solvent, such as acetic acid and water, with oxygen-containing gas, in the presence of a catalyst system comprising cobalt atoms, manganese atoms, zirconium atoms, and bromine atoms, wherein the weight ratio of cobalt to manganese is from about 10 to about 400. The processes may be carried out at temperatures, for example, from about 125° to about 155° C., or from about 130° C. to about 155° C., or from 130° to 150° C.

According to the invention, the zirconium atoms may be present in an amount, for example, of at least about 25 ppm, or at least 50 ppm, or at least 100 ppm, up to about 1000 ppm, or up to about 1250 ppm, or up to about 1500 ppm. The processes according to the invention produce one or more aromatic dicarboxylic acids as a reaction product, with good conversions, such as, in those embodiments in which p-xylene is the reactant, a concentration of 4-carboxybenzaldehyde (4CBA), based on the weight of terephthalic acid produced, of less than 6 wt. %, or less than 5 wt. %, or less than 3 wt. %, or less than 1 wt. %, while obtaining reduced carbon oxides formation, for example no more than about 1.2 moles $CO_X$, or no more than about 0.6 mole $CO_X$, or no more than about 0.3 mole $CO_X$, in each case with respect to the molar quantity of dialkyl aromatic compounds fed to the reactor.

Thus, in one embodiment, the process comprises oxidizing a dialkyl aromatic in the liquid phase. The liquid phase may at any moment comprise any or all of: the feed reactants p-xylene and the oxygen-containing gas, the solvent, the catalyst composition, and the dicarboxylic acid reaction product dissolved or suspended in the reaction mixture, especially when the process is carried out as a continuous process. The products of the processes according to this embodiment include the dicarboxylic acid solids as the predominant product (for example, at least 50 wt. % of the solids), and incomplete oxidation products which may be found in the solids, in the liquid phase, or in both. The dialkyl aromatic fed to the oxidation reactor may be purified of contaminants which may interfere with the oxidation reaction. The reactant feed may be pure or a mix of the compound isomers or lower or higher homologues, as well as some saturated alicyclic or aliphatic compounds having similar boiling points to the aromatic or fused ring compounds. However, in this embodiment, at least 80 wt. %, preferably at least 95 wt. %, or at least 98 wt. % of the liquid reactants is the dialkyl aromatic reactant.

According to the invention, the liquid phase oxidation processes are carried out in the presence of an aliphatic solvent. Suitable solvents are those which are solvents for the dialkyl aromatics under the oxidation reaction conditions, and especially those in which the dicarboxylic acid products form a pumpable crude flow discharged from the oxidation reactor. Suitable solvents include mixtures of water and the aliphatic solvents. The preferred aliphatic solvents are aliphatic carboxylic acids, and include aqueous solutions of $C_2$ to $C_6$ monocarboxylic acids, and preferably $C_2$ to $C_4$ monocarboxylic acids, e.g., acetic acid, propionic acid, n-butyric acid, isobutyric acid, n-valeric acid, trimethylacetic acid, caprioic acid, and mixtures thereof. Preferably, the solvent is volatile under the oxidation reaction conditions to allow it to be taken as an off-gas from the oxidation reactor. It is also preferred that the solvent selected is one in which the catalyst composition is soluble under the reaction conditions.

A preferred solvent for use according to the invention is an aqueous acetic acid solution, having a concentration, for example, from about 90 to about 97 wt. % acetic acid, based on the weight of the liquid phase of the reaction medium. In various embodiments, the solvent comprises a mixture of water and acetic acid which, for example, has a water content sufficient to provide at least about 3.0% by weight water in the reaction medium, or at least 4.0 wt. %, or from about 3.0 wt. % to about 15 wt. %, or from 3 wt. % to 11 wt. %.

The crude dicarboxylic acid composition may be discharged from the oxidation zone and subjected to a variety of mother liquor exchange, separation, purification, or recovery methods. These methods can provide recovered solvent and catalyst composition for recycling back to the oxidation zone.

Thus, a portion of the solvent feed to the primary oxidation reactor may be obtained from a recycle stream obtained by displacing, for example, from about 80 to 90% of the mother liquor taken from the crude reaction mixture stream discharged from the primary oxidation reactor with fresh, wet acetic acid. This exchange may be accomplished in any convenient apparatus but can most easily be accomplished in a centrifuging apparatus, such as one or more cyclones.

The processes according to the invention are conducted in the presence of a source of oxygen. This may be accomplished by feeding an oxygen-containing gas to the oxidation reactor to allow the gas to contact the liquid reaction mixture in the reactor. The predominately gas-phase oxidant stream introduced into the reactor comprises molecular oxygen ($O_2$), for example in the range from about 5 to about 100 mole percent molecular oxygen, or from about 10 to about 50 mole percent molecular oxygen, or from 15 to 25 mole percent molecular oxygen. The balance of the oxidant stream typically is comprised primarily of a gas or gases, such as nitrogen, that are inert to oxidation. Thus, the oxidant stream may comprise dry air containing about 21 mole percent molecular oxygen and substantial amounts of nitrogen.

The presence or absence of carbon dioxide in the oxidant stream is not seen to be especially critical, and may thus vary within a broad range, from substantially no carbon dioxide, to that amount of carbon dioxide normally found in fresh air (about 0.05 wt. %), or up to about 1 wt. %, or up to 2 wt. %, or up to 4 wt. %, or even greater amounts.

In the processes according to the invention, the oxidation reaction proceeds at elevated temperatures and pressures, so that at least a portion of the reaction mixture is in the liquid phase. During oxidation, the time-averaged and volume-averaged temperature of the reaction medium may be maintained, for example, in the range from about 125° C. to about 155° C., or from about 130° C. to about 155° C., or from 130° C. to 150° C. The overhead pressure above the reaction medium may, for example, be maintained in the range of from about 1 to about 40 bar gauge (barg), or from about 2 to about 20 barg, or from 2 to 8 barg.

We have found according to the invention that relatively moderate oxidation temperatures, such as from about 125° C. to about 155° C., help to reduce the extent of carbon oxides formation, believed to represent in part the extent of solvent burn. The processes of the invention thus are particularly well suited for oxidizing p-xylene at relatively moderate temperatures, as already described.

The catalyst compositions employed in the processes of the invention comprise cobalt atoms, manganese atoms, zirconium atoms, and bromine atoms, supplied by any suitable means, as further described below. In a preferred embodiment, the catalyst compositions consist essentially of cobalt atoms, manganese atoms, zirconium atoms, and bromine atoms. The catalyst composition is typically soluble in the solvent under reaction conditions, or it is soluble in the reactants fed to the oxidation zone. Preferably, the catalyst composition is soluble in the solvent at 40° C. and 1 atm, and is soluble in the solvent under the reaction conditions.

The cobalt atoms may be present, for example, in an amount of at least 500 ppm, or at least 750 ppm, or at least 1,000 ppm, or from about 500 ppm to about 6,000 ppm, or from 750 ppm to 4,500 ppm, or from 1,000 ppm to 4,000 ppm, in each instance with respect to the weight of the liquid in the reaction medium. The cobalt atoms may be provided in ionic form as inorganic cobalt salts, such as cobalt bromide, cobalt nitrate, or cobalt chloride, or organic cobalt compounds such as cobalt salts of aliphatic or aromatic acids having 2-22 carbon atoms, including cobalt acetate, cobalt octanoate, cobalt benzoate, cobalt acetylacetonate, and cobalt naphthalate.

The weight amounts of each of cobalt, manganese, zirconium, and bromine are based on the atomic weight of the atoms, whether or not the atoms are in elemental form or in ionic form. For example, the amount of cobalt refers to the amount of cobalt atoms, whether elemental or ionic, and not the amount of cobalt acetate. The stated concentrations of catalyst components are based on the quantity of catalyst components in the liquid portion of the reaction medium in the oxidation reactor. The catalyst component concentrations may be measured, for example, by sampling the oxidation reactor.

The oxidation state of cobalt when added as a compound to the reaction mixture is not limited, and includes both the +2 and +3 oxidation states.

The manganese atoms may be provided as one or more inorganic manganese salts, such as manganese borates, manganese halides, manganese nitrates, or organometallic manganese compounds such as the manganese salts of lower aliphatic carboxylic acids, including manganese acetate, and manganese salts of beta-diketonates, including manganese acetylacetonate. Manganese of the catalyst composition may be present in a concentration from about 20 to about 425 ppm, or from 20 to 300 ppm, or from 20 to 200 ppm.

The zirconium may be provided as zirconium oxide or as one or more inorganic zirconium salts, such as zirconium chloride, zirconium bromide, and zirconium sulfate, or organometallic zirconium compounds such as zirconium acetate, zirconium acetate hydroxide, zirconium acetylacetonate, zirconium butoxide, zirconium propoxide or zirconyl acetate. The zirconium atoms of the catalyst composition may be present in an amount of at least 25 ppm, or at least 50 ppm, or at least 100 ppm, up to about 1000 ppm, or up to about 1250 ppm, or up to about 1500 ppm. Suitable ranges may thus vary from about 25 ppm to about 1500 ppm, or from 50 ppm to 1250 ppm, or from 100 ppm to 1000 ppm.

The bromine component may be added as elemental bromine, in combined form, or as an anion. Suitable sources of bromine include but are not limited to hydrobromic acid, sodium bromide, ammonium bromide, potassium bromide, tetrabromoethane, benzyl bromide, alpha-bromo-p-toluic acid, and bromoacetic acid. Hydrobromic acid, sodium bromide, or alpha-bromo-p-toluic acid may be preferred bromine sources. Bromine may thus be present in an amount ranging from about 750 to about 6,000 ppm, based on the total liquid in the reaction medium, or from 900 ppm to 5000 ppm, or from 1000 to 4500 ppm, each with respect to the total weight of liquid in the reaction medium.

According to the invention, the relative amounts of elements in the catalyst composition are selected so as to achieve acceptable conversion, while limiting acid burn. Thus, the weight ratio of cobalt atoms to bromine atoms may be, for example, from about 0.6 to about 10, or from 0.7 to 8, or from 0.8 to 5.

In an important aspect of the invention, the ratio of cobalt atoms to manganese atoms may be from about 10.0 to about 400, or from about 12 to about 300, or from about 15 to about 250. In various other embodiments, the ratio of cobalt atoms to manganese atoms will be at least about 10, or at least 12, or at least 15, or at least 18, up to about 150, or up to about 200, or up to about 300, or up to about 400.

Other organic or non-metallic catalyst components can be included in the catalyst composition of the invention, or the processes may be carried out in the substantial absence of additional organic or non-metallic catalysts. For example, the catalyst composition may include a source of pyridine. The pyridine component of the catalyst composition may be added to a primary oxidation reactor or to post oxidation reactors. The pyridine component can be in the form of pyridine per se or in the form of a compound of pyridine.

Further, the processes according to the invention may be carried out in the presence of, or in the substantial absence of, one or more aldehydes or ketones.

Further, the processes according to the invention may be carried out in the presence of additional metal atoms, or in the substantial absence thereof, so long as the catalyst composition comprises cobalt atoms, manganese atoms, and zirconium atoms, with bromine atoms provided as a promoter. Such additional metals may include, but not be limited to, molybdenum, sodium, potassium, copper, hafnium, chromium, cerium, iron, tungsten, bismuth, vanadium, and palladium.

The catalyst composition can be formed by adding each source to the oxidation reactor separately, in sequence, or simultaneously, or a prepared composition may be added to the oxidation reactor, and in either case, the addition may be made as an initial batch or continuously during the course of the oxidation reaction. The catalyst composition prepared as a batch may be dissolved in the solvent to form a catalyst feed followed by adding the catalyst feed to the primary oxidation reactor. Each component, or the catalyst composition batch, can be added to the primary oxidation reactor before, during, or after addition of the solvent. In a continuous process, the catalyst components or the catalyst composition may be added simultaneous with the solvent feed, or in the solvent feed, or separately metered as required for fresh make-up.

After the initial charge of catalyst composition in a continuous process, the residual mother liquor from the primary oxidation may supply a portion of the necessary catalyst components to the primary oxidation reactor by partial displacement of the primary oxidation mother liquor with fresh solvent. The remainder can be made up with a continuous fresh feed of make-up catalyst.

In the processes according to the invention, the extent of solvent burned and rendered unusable as a recycle stream may be reduced relative to typical processes. While the absolute amount of solvent burn in the present invention may be reduced, this reduction is not achieved at the expense of acceptable conversion. Obtaining a low amount of carbon oxides formation might be achieved by running the reaction at low oxidation temperatures or using a less active catalyst, but this typically results in lowered conversion and increased quantities of intermediates. The processes of the invention have the advantage of maintaining a low carbon oxides formation while minimizing the impact on conversion.

Thus, in a preferred embodiment, the amount of carbon oxides formation (in total moles of CO and $CO_2$, expressed as COx per mole of dialkyl aromatic compounds fed to the reactor) is no more than about 1.2 moles COx/mole, or no more than about 0.6, or no more than about 0.3 mole $CO_x$ per mole of dialkyl aromatic compounds fed to the reactor.

Thus, in a process in accordance with the present invention, p-xylene, in an amount, for example, from about 2 to about 15 wt. %, based on the weight of liquid in the reaction medium, is combined with acetic acid, and an oxygen-containing gas, at a temperature from about 125° C. to about 155° C., using a catalyst composition comprising cobalt atoms, manganese atoms, and zirconium atoms, with bromine atoms provided as a promoter, wherein the weight ratio of cobalt to manganese is from about 10 to about 400, and wherein the zirconium atoms are present in an amount of at least 25 ppm, or at least 50 ppm, up to about 1000 ppm, or up to about 1500 ppm.

Figure 1:
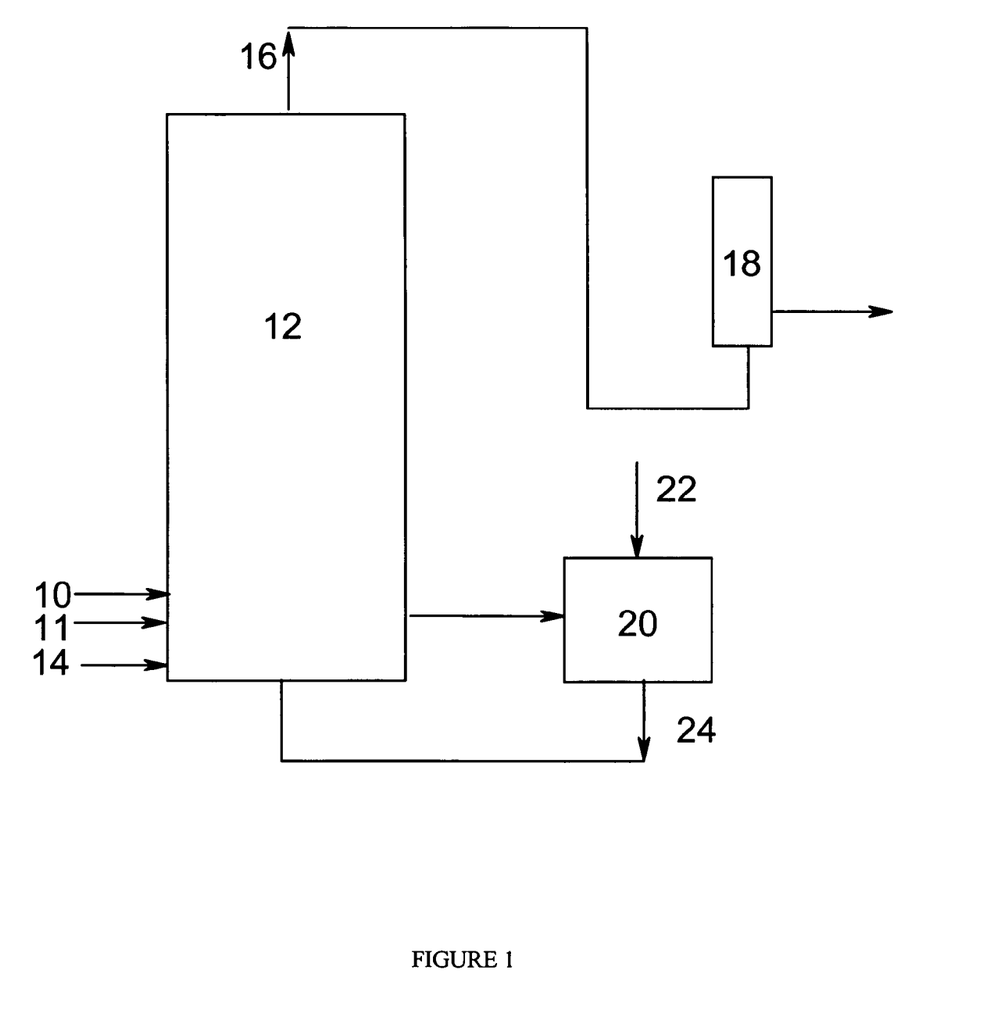
FIG. 1 illustrates a process flow of crude terephthalic acid streams and the overhead of an oxidation unit.

An embodiment of the invention will now be described referring to the accompanying FIG. 1, in which p-xylene is introduced via conduit 10 into primary oxidation reactor 12, and aqueous acetic acid solvent having dissolved therein the catalyst composition of the invention fed through line 11 to the reactor 12. If desired, the p-xylene, solvent, and catalyst composition charges may be fed to reactor 12 at a plurality of points, or fed together through one line. An oxygen-containing gas under pressure is introduced near the bottom of the reactor 12 via conduit 14. The preferred oxygen-containing gas is air or oxygen-enriched air. The flow rate of the oxygen-containing gas to reactor 12 is controlled to maintain between about 2 and 9 volume percent oxygen (calculated on a dry, solvent free basis) in the off-gas which exits the reactor via conduit 16. The reactants in reactor 12 are maintained at an elevated pressure of about 50 to 175 psia to maintain a contained, volatizable reaction medium substantially in the liquid state at the reaction temperature of about 125° C. to about 155° C.

During the course of the oxidation reaction, exothermic heat of reaction and water generated by the oxidation of p-xylene are removed from reactor 12 by vaporization of a portion of the liquid reaction medium. These vapors, known as reactor off-gas, comprise vaporized acetic acid solvent, about 5 to 30 weight percent water, and oxygen-depleted process gas containing minor amounts of decomposition products including catalyst residue, as well as additional carbon dioxide and carbon monoxide generated by the decomposition of acetic acid. The reactor off-gas passes upwardly through the reactor 12 and is conveyed via conduit 16 to the lower portion of water removal column 18 for distillation and recovery of the acetic acid back to the primary oxidation reactor. The crude reaction mixture is discharged from the primary oxidation reactor to a solid/liquid separator 20 into which is fed fresh acetic acid through line 22 to exchange the mother liquor discharged through line 24. The mother liquor containing acetic acid and the catalyst composition is subjected to conventional purification and purging techniques to recover and recycle the catalyst composition to the primary oxidation reactor 12.

Suitable dialkyl aromatic compounds useful as reactor feed-mixture components or ingredients in the methods of the present invention include dialkyl benzenes and naphthalenes such as o-xylene, m-xylene, p-xylene, 2,6-dimethylnaphthalene, 2,7-dimethylnaphthalene and 2,6-diisopropylnaphthalene. The respective aromatic carboxylic acid products of these alkyl aromatic compounds are orthophthalic acid, isophthalic acid, terephthalic acid (TPA), and 2,6- and 2,7-naphthalenedicarboxylic acids. The processes of the invention can be used to produce TPA and isophthalic acid, and are particularly well suited for the production of benzenedicarboxylic and naphthalenedicarboxylic acids, especially TPA.

Suitable aqueous aliphatic acid solvents useful in the methods of the invention are those that are readily volatilizable at the reaction temperatures. Among such solvents are aqueous solutions of $C_2$ to $C_6$ monocarboxylic acids, e.g., acetic acid, propionic acid, n-butyric acid, isobutyric acid, n-valeric acid, trimethylacetic acid, caprioic acid, and mixtures thereof. Preferably, the volatilizable monocarboxylic aliphatic acid solvent is an aqueous acetic acid solution.

Further description of the oxidation of alkyl aromatics to benzenepolycarboxylic acids may be found in the "Phthalic Acids and Other Benzenepolycarboxylic Acids" entry of Kirk-Othmer *Encyclopedia of Chemical Technology*, Vol 18, 4th ed., (1995) pp. 991-1043, the relevant portions of which are incorporated herein by reference.

The measure of 4-carboxybenzaldehyde (4CBA) in the product mixture from the oxidation of p-xylene to terephthalic acid, being an incomplete oxidation product, is understood to indicate the degree of conversion achieved, with lower 4CBA levels indicating higher conversion.

As described, the acetic acid solvent is decomposed, to some extent, in a side reaction to produce mainly carbon dioxide, carbon monoxide, and methyl acetate. The total oxidative decomposition products were estimated in the examples by measuring the number of moles of carbon dioxide and carbon monoxide exiting in the oxidizer vent gas. To achieve satisfactory results for the oxidation process, the amount of carbon oxides formation should be minimal while the rate of xylene conversion to TPA is maximized (the concentration of 4CBA in the product mixture is low). Thus, the amount of 4CBA found in the oxidizer filtrate is a measure of the rate of the oxidation, and the amount of carbon oxides in the vent gas is a measure of cost of the oxidation process.

The invention has been described in detail with particular reference to preferred embodiments thereof, but it will be understood that variations and modifications can be effected within the spirit and scope of the invention. Moreover, all patents, patent applications (published or unpublished, foreign or domestic), literature references or other publications noted above are incorporated herein by reference for any disclosure pertinent to the practice of this invention.

EXAMPLES

Examples 1-41

In Examples 1-41, a solution containing the catalyst components in concentrations described in Table 1 was prepared and 60 grams of the solution was transferred to the autoclave. Cobalt, manganese and zirconium were provided as cobalt(II) acetate hydrate, manganese(II) acetate hydrate and zirconium acetate hydroxide, respectively. Bromine was added as hydrobromic acid and sodium bromide in ratios found in Table 1. The autoclave was pressurized with approx. 20 bar nitrogen (ca. 290 psi) and then the catalyst solution was heated up to the reaction temperature under stirring at 2000 rpm.

At reaction temperature, the air flow diluted down to 10% oxygen in nitrogen for safety reasons was started at a total gas flow of 1.13 NL/min and the reaction pressure was adjusted to the desired total pressure to ensure a fairly constant oxygen partial pressure. Then the para-xylene feeding (140 μL/min) was started (this is t=0 for the reaction time). Thirty seconds after the start of the para-xylene feeding, 0.25 mmol peracetic acid in 1.5 ml acetic acid was introduced into the solution to start the reaction.

The para-xylene feeding was stopped 30 min after the start. Subsequently the gas flow was stopped, and the system was cooled down. The autoclave was then depressurized and the reaction solution was filtered to isolate the CTA. The yield of the filtrate was recorded. The CTA was washed two times with 25 ml of acetic acid (96%) and then once with 40 ml methanol. The washed CTA was dried at 60° C. and then weighed.

The off-gas was analyzed with respect to $CO_2$ and CO by ND-IR (ABB, Advanced Optima) and $O_2$ by a paramagnetism detection system (Hartmann & Braun, Magnos 6G). The composition of the solid isolated and the filtrate was determined by high-pressure liquid chromatography.

TABLE 1

Results from semi-batch reaction Examples 1-41 performed as described above.

| Example | Co ppm | Mn ppm | Br (as HBr) ppm | Br (as NaBr) ppm | Zr ppm | T °C. | H2O % | Pressure bar | Yld % | CO$_x$ mol/min | 4CBA(S) ppm | BA(F) ppm |
|---|---|---|---|---|---|---|---|---|---|---|---|---|
| 1 | 1800 | 80 | 1950 | 0 | 230 | 135 | 4 | 17.4 | 33 | 0.000043 | 56430 | 59 |
| 2 | 1800 | 80 | 1950 | 0 | 300 | 160 | 4 | 19.0 | 88 | 0.000314 | 1390 | 157 |
| 3 | 1800 | 80 | 1950 | 0 | 460 | 140 | 4 | 17.7 | 88 | 0.000111 | 14590 | 132 |
| 4 | 1800 | 80 | 1950 | 0 | 460 | 170 | 4 | 19.9 | 90 | 0.000657 | 620 | 220 |
| 5 | 3000 | 132 | 1800 | 1450 | 300 | 160 | 4 | 19.0 | 86 | 0.000393 | 1970 | 46 |
| 6 | 2000 | 88 | 1800 | 366 | 610 | 145 | 4 | 17.9 | 92 | 0.000169 | 5510 | 102 |
| 7 | 1000 | 44 | 1083 | 0 | 300 | 130 | 4 | 17.2 | 12 | 0.000039 | 51980 | 43 |
| 8 | 1000 | 44 | 1083 | 0 | 610 | 145 | 4 | 17.9 | 28 | 0.000082 | 44130 | 62 |
| 9 | 2000 | 88 | 1800 | 366 | 610 | 160 | 4 | 19.0 | 91 | 0.000637 | 630 | 98 |
| 10 | 3000 | 132 | 1800 | 1450 | 910 | 130 | 4 | 17.2 | 87 | 0.000093 | 21890 | 65 |
| 11 | 2000 | 88 | 1800 | 366 | 300 | 145 | 4 | 17.9 | 85 | 0.000140 | 7180 | 90 |
| 12 | 2000 | 88 | 1800 | 366 | 610 | 145 | 4 | 17.9 | 90 | 0.000206 | 4630 | 102 |
| 13 | 3000 | 132 | 1800 | 1450 | 910 | 160 | 4 | 19.0 | 89 | 0.000601 | 1130 | 104 |
| 14 | 3000 | 132 | 1800 | 1450 | 300 | 130 | 4 | 17.2 | 56 | 0.000060 | 56430 | 57 |
| 16 | 2000 | 88 | 1800 | 366 | 910 | 145 | 4 | 17.9 | 89 | 0.000234 | 3430 | 84 |
| 17 | 3000 | 132 | 1800 | 1450 | 610 | 145 | 4 | 17.9 | 86 | 0.000184 | 5720 | 70 |
| 18 | 2000 | 88 | 1800 | 366 | 610 | 130 | 4 | 17.2 | 75 | 0.000073 | 36830 | 62 |
| 19 | 1000 | 44 | 1083 | 0 | 300 | 160 | 4 | 19.0 | 85 | 0.000329 | 2920 | 177 |
| 20 | 2000 | 88 | 1800 | 366 | 610 | 145 | 4 | 17.9 | 86 | 0.000204 | 4690 | 82 |
| 21 | 1000 | 44 | 1083 | 0 | 910 | 160 | 4 | 19.0 | 45 | 0.000562 | 21480 | 150 |
| 22 | 2000 | 88 | 1800 | 366 | 610 | 145 | 8 | 18.0 | 91 | 0.000195 | 5020 | 109 |
| 23 | 3000 | 132 | 1800 | 1450 | 610 | 145 | 6 | 18.0 | 87 | 0.000201 | 5880 | 96 |
| 24 | 3000 | 132 | 1800 | 1450 | 910 | 130 | 8 | 17.2 | 80 | 0.000108 | 30930 | 71 |
| 25 | 3000 | 132 | 1800 | 1450 | 300 | 160 | 8 | 19.1 | 88 | 0.000303 | 2830 | 111 |
| 26 | 2000 | 88 | 1800 | 366 | 610 | 145 | 6 | 18.0 | 88 | 0.000219 | 4330 | 100 |
| 27 | 1000 | 44 | 1083 | 0 | 910 | 130 | 8 | 17.2 | 4 | 0.000047 | 53540 | 28 |
| 28 | 2000 | 88 | 1800 | 366 | 610 | 130 | 6 | 17.2 | 64 | 0.000075 | 42970 | 69 |
| 29 | 1000 | 44 | 1083 | 0 | 300 | 160 | 8 | 19.1 | 89 | 0.000388 | 1150 | 195 |
| 30 | 2000 | 88 | 1800 | 366 | 910 | 145 | 6 | 18.0 | 93 | 0.000229 | 4140 | 132 |
| 31 | 1000 | 44 | 1083 | 0 | 910 | 160 | 8 | 19.1 | 67 | 0.000365 | 14040 | 164 |
| 32 | 1000 | 44 | 1083 | 0 | 300 | 130 | 8 | 17.2 | 20 | 0.000046 | n.d. | 46 |
| 33 | 2000 | 88 | 1800 | 366 | 610 | 160 | 6 | 19.1 | 93 | 0.000493 | 860 | 150 |
| 34 | 3000 | 132 | 1800 | 1450 | 910 | 160 | 8 | 19.1 | 86 | 0.000513 | 1310 | 106 |
| 35 | 2000 | 88 | 1800 | 366 | 300 | 145 | 6 | 18.0 | 86 | 0.000145 | 6960 | 95 |
| 36 | 1000 | 44 | 1083 | 0 | 610 | 145 | 6 | 17.9 | 20 | 0.000081 | 45060 | 56 |
| 37 | 3000 | 132 | 1800 | 1450 | 300 | 130 | 8 | 17.2 | 67 | 0.000078 | 44750 | 73 |
| 38 | 2000 | 88 | 1800 | 366 | 610 | 145 | 6 | 17.9 | 81 | 0.000166 | 12330 | 94 |
| 39 | 2000 | 88 | 1800 | 366 | 610 | 145 | 6 | 17.9 | 77 | 0.000166 | 12280 | 93 |
| Comp. Ex. 40 | 1800 | 80 | 1950 | 0 | 0 | 160 | 6 | 19.0 | 86 | 0.000210 | 3500 | 130 |
| Comp. Ex. 41 | 1800 | 50 | 2000 | 0 | 0 | 140 | 4 | 17.7 | 48 | 0.000040 | 74100 | 90 |

Yld (yield) is reported for the dried isolated solid assuming the quantitative conversion of the p-xylene fed into terephthalic acid;
CO$_x$ is the sum of CO and CO$_2$ measured in the off-gas.
4CBA(S) is the concentration of 4CBA found in the dry isolated solid;
BA(F) is the concentration of benzoic acid found in the filtrate.

The many features and advantages of the invention are apparent from the detailed specification and, thus, it is intended by the appended claims to cover all such features and advantages of the invention which fall within the true spirit and scope of the invention. Further, since numerous modifications and changes will readily occur to those skilled in the art, it is not desired to limit the invention to the exact construction and operation illustrated and described, and accordingly all suitable modifications and equivalents may be resorted to, falling within the scope of the invention.

We claim:

1. A process for producing an aromatic dicarboxylic acid, the process comprising combining in a reaction medium a dialkyl aromatic, a solvent comprising water and a saturated organic acid having from 2-4 carbon atoms, and an oxygen-containing gas, at a temperature from 130° C. to 150° C., in the presence of a catalyst composition comprising cobalt, manganese, zirconium, and bromine, wherein the weight ratio of cobalt to manganese in the reaction mixture is from about 10 to about 400, wherein zirconium is present in an amount ranging from 300 ppm to 1500 ppm with respect to the weight of the liquid in the reaction medium.

2. The process according to claim 1, wherein the weight ratio of cobalt to manganese in the reaction mixture is from about 12 to about 300.

3. The process according to claim 1, wherein the weight ratio of cobalt to manganese in the reaction mixture is from about 15 to about 250.

4. The process according to claim 1, wherein the dialkyl aromatic comprises p-xylene and the aromatic dicarboxylic acid produced comprises terephthalic acid.

5. The process according to claim 1, wherein the saturated organic acid comprises acetic acid.

6. The process according to claim 1, wherein the zirconium is provided as one or more of: zirconium oxide, zirconium bromide, zirconium chloride, zirconium acetate, zirconium acetate hydroxide, zirconium acetylacetonate, zirconium hydroxide, zirconium butoxide, zirconium propoxide, or zirconyl acetate.

7. The process according to claim 1, wherein the zirconium is provided as zirconium acetate, zirconium acetate hydroxide, or zirconyl acetate.

8. The process according to claim 1, wherein the oxygen-containing gas comprises air.

9. The process according to claim 1, wherein the cobalt is provided in an amount from about 500 ppm to about 6,000 ppm, with respect to the weight of liquid in the reaction medium.

10. The process according to claim 1, wherein the cobalt is provided in an amount from about 750 ppm to about 4,500 ppm, with respect to the weight of liquid in the reaction medium.

11. The process according to claim 1, wherein the cobalt is provided in an amount from about 1,000 ppm to about 4,000 ppm, with respect to the weight of liquid in the reaction medium.

12. The process according to claim 1, wherein the manganese is provided in an amount from about 20 ppm to about 425 ppm, with respect to the weight of liquid in the reaction medium.

13. The process according to claim 1, wherein the manganese is provided in an amount from about 20 ppm to about 300 ppm, with respect to the weight of liquid in the reaction medium.

14. The process according to claim 1, wherein the manganese is provided in an amount from about 20 ppm to about 200 ppm, with respect to the weight of liquid in the reaction medium.

15. The process according to claim 1, wherein the bromine is provided in an amount from about 750 ppm to about 6,000 ppm, with respect to the weight of liquid in the reaction medium.

16. The process according to claim 1, wherein the bromine is provided in an amount from about 900 ppm to about 5,000 ppm, with respect to the weight of liquid in the reaction medium.

17. The process according to claim 1, wherein the bromine is provided in an amount from about 1,000 ppm to about 4,500 ppm, with respect to the weight of liquid in the reaction medium.

18. The process according to claim 1, wherein the weight ratio of cobalt to bromine is from about 0.6 to about 10.

19. The process according to claim 1, wherein the weight ratio of cobalt to bromine is from about 0.7 to about 8.

20. The process according to claim 1, wherein the weight ratio of cobalt to bromine is from about 0.8 to about 5.

21. The process according to claim 1, wherein the process produces no more than about 1.2 moles $CO_X$ per mole of dialkyl aromatic provided to the reaction medium.

22. The process according to claim 1, wherein zirconium is present in an amount of at least 460 ppm with respect to the weight of the liquid in the reaction medium.

23. The process according to claim 1, wherein zirconium is present in an amount of at least 610 ppm with respect to the weight of the liquid in the reaction medium.

24. The process according to claim 1, wherein zirconium is present in an amount in the range of from about 460 to about 1,250 ppm with respect to the weight of the liquid in the reaction medium.

25. The process according to claim 1, wherein zirconium is present in an amount in the range of from about 610 to about 1,000 ppm with respect to the weight of the liquid in the reaction medium.

\* \* \* \* \*